United States Patent [19]
Heinonen

[11] Patent Number: 5,918,596
[45] Date of Patent: Jul. 6, 1999

[54] SPECIAL GAS DOSE DELIVERY APPARATUS FOR RESPIRATION EQUIPMENT

[75] Inventor: Erkki Heinonen, Helsinki, Finland

[73] Assignee: Instrumentarium Corp., Helsinki, Finland

[21] Appl. No.: 08/841,466

[22] Filed: Apr. 22, 1997

[51] Int. Cl.⁶ ........................................... A62B 7/00
[52] U.S. Cl. .............................. 128/204.21; 128/204.22; 128/205.11
[58] Field of Search .................. 128/204.21, 204.22, 128/204.23, 204.28, 205.23, 203.12, 203.25, 205.24, 205.11

[56] References Cited

U.S. PATENT DOCUMENTS

| | | | |
|---|---|---|---|
| 5,423,313 | 6/1995 | Olsson et al. ................... | 128/204.21 |
| 5,485,827 | 1/1996 | Zapol et al. . | |

FOREIGN PATENT DOCUMENTS

| | | |
|---|---|---|
| 589751 | 3/1994 | European Pat. Off. . |
| 621051 | 10/1994 | European Pat. Off. . |
| 640356 | 3/1995 | European Pat. Off. . |
| 640357 | 3/1995 | European Pat. Off. . |
| 659445 | 6/1995 | European Pat. Off. . |
| 43 27 730 | 3/1995 | Germany . |

OTHER PUBLICATIONS

Nitrogen dioxide ($NO_2$) production for different doses of inhaled nitric oxide (NO) during mechanical ventilation with different tidal volumes using two prototypes for the administration of NO, R. Kuhlen et al., *Critical Care*, 1997, vol. 1. Suppl. 1, P49.

*Primary Examiner*—John G. Weiss
*Assistant Examiner*—Charles W. Anderson
*Attorney, Agent, or Firm*—Andrus, Sceales, Starke & Sawall

[57] ABSTRACT

A special gas dose delivery unit for respiratory equipment has a special gas flow conduit connected to a special gas source. The unit includes a supply of carrier gas for the special gas, preferably obtained by withdrawing gas from the inspiration limb of the patient breathing circuit. A valve, controllable in accordance with desired special gas dose parameters and the breathing pattern of the patient, injects the special gas into the carrier gas for provision to the outlet conduit of the special gas dose delivery unit. The outlet conduit is connected to the patient limb of the breathing circuit for delivery to the patient.

30 Claims, 2 Drawing Sheets

SPECIAL GAS DOSE DELIVERY APPARATUS FOR RESPIRATION EQUIPMENT

BACKGROUND OF THE INVENTION

In respirator treatment, a patient is connected to a respirator, which aids the patient in breathing. The respirator typically comprise a means of mixing and forming a breathing gas having a predetermined ratio of one or more gases, the pressurized sources for which are connected to the respirator. The gas mixture has to contain a sufficient amount of oxygen. For this reason, one of the gases is always $O_2$, or alternatively, in the most simplified one gas source devices, is air. The other gas or gases to be mixed with $O_2$ comprise most typically air, $N_2O$, and sometimes also He or Xe.

To perform the mixing function, each of the gas flow paths has a regulating means, typically a valve, to regulate the gas flow. In current state of the art, these regulating means are driven by a microprocessor control unit according to the information the control unit receives from various pressure, flow, and/or position sensors to regulate to predetermined control parameter values.

The control parameters include a plurality of various criteria defining the respiration pattern. These parameters are e.g. inspiration and expiration times, respiration rate, tidal volume (the volume of one breath), inspiratory flow, inspiration pressure, and positive end expiratory pressure. Modern respirator treatment encourages the patient to breathe by himself. State of the art respirators are thus equipped to both support the spontaneous breath trials by the patient and to provide pressure to assist or carry out breathing when necessary.

The patient is connected to the respirator through a breathing circuit comprising an inspiratory limb, expiratory limb, and a patient limb terminating in an endotracheal tube or breathing mask. These elements are connected together at a Y-piece connector. The inspiratory limb is connected to the respirator at the outlet for the breathing gas mixture and to the inlet of the Y-piece connector. The expiratory limb is connected to the outlet of the Y-piece connector and to a expiration valve, normally also included in the respirator. The patient is connected to the breathing circuit through the patient limb to the endotracheal tube or breathing mask.

When the patient is inspiring, the expiration valve is closed. The breathing gas is supplied with overpressure through the inspiratory limb to endotracheal tube or breathing mask and further to the lungs of the patient. During expiration, an inspiratory valve also included in the respirator is closed, and the expiration valve is opened, releasing the pressure within the lungs. This relief is based on the tension and elasticity of the lungs.

Tidal volumes range from a few tens of milliliters for the smallest babies to more than one liter for adults. The respiration rates also vary from tens/minute down to a few/minute. Typical breathing gas flow rates extend from the level of one liter/min up to 10 liters/min, but may even exceed these. The volume of breathing gas is delivered during the inspiration phase, representing typically one third of the respiration cycle. Thus the peak inspiratory flow may easily exceed 30 liters/min and reach momentarily 100 liters/min in inspiratory regulation based on a preset inspiration pressure.

During respirator treatment, for diagnostic and therapeutic purposes, a need for completing the breathing gas with a special gas exists. Typical special gases are nitric oxide (NO) for improvement of lung perfusion and thus patient $O_2$ uptake raising the blood oxygen saturation, $SF_6$ (sulfur hexa fluoride) for measuring the lung functional residual volume (FRC) and nitrous oxide ($N_2O$) for measuring the lung capillary blood flow. The gases may even be combined into a single gas reservoir for multiple action behavior as shown e.g. in EP 640357.

A special problem arises from the supply of, or dosing, NO due to the extremely small amounts of gas to be regulated. The usual levels start from 0.1 ppm (part per million) up to some tens of ppm. To facilitate the regulation, the NO gas is diluted to a ratio about 100 ppm-1000 ppm in $N_2$ in the pressure container from which the gas is delivered. Another problem is the reactivity of the NO. Together with $O_2$ an extremely toxic end product, nitrogen dioxide ($NO_2$), will be produced from the NO. To minimize this production, it is advantageous to design the delivery system to minimize the exposure time the NO and $O_2$ have to react with each other.

A further requirement for an advantageous form of the delivery system comes from user ergonomy. The personnel taking care of the patient often work near the mouth of the patient and with the above described breathing circuit. The less additional equipment required in this area, the better the equipment will be from the ergonometric standpoint.

State of the art technology includes various delivery systems to deliver the special gas in preset amounts through the breathing circuitry to the patient. The delivery systems are fitted with the respiratory breath circuitry. The delivery system may operate either continuously or synchronously with inspiration. EP 640356 presents a continuous flow delivery system for spontaneously breathing patients. In this system the special gas is mixed with the breathing gas in the gas mixer. The breathing circuit is modified with a connecting tube. Both the inspiratory and expiratory limbs are connected to this connecting tube. Thus, the patient inhales the gas through the inspiratory limb from the connecting tube and exhales through the expiratory limb to the connection tube. The mixer delivers a continuous flow of breathing gas with an added, predetermined concentration of the special gas, to the connecting tube. In the delivery system, the continuous flow is set to 20 liters/min to fulfill peak flow requirements. Even larger peak flows are possible as the backflow from the connecting tube. The relatively high flow rate is used to minimize the reaction time of NO and $O_2$ and to minimize the risk of rebreathing the gas the patient has already expired through the connecting tube. The arrangement solves the forementioned problems of the NO delivery, but due to the high flow, this arrangement causes a very large loss of breathing gas and NO. Particularly, the NO may be very expensive causing also economic losses. Due to the toxicity of NO and the end product $NO_2$, an evacuation system is a prerequisite for safe operation. Further, this arrangement does not solve the delivery problems with patients requiring breathing aid from respirator.

A delivery system in connection with a respirator is shown in EP 640357. The system described is for delivery of special gas, which in this case is a mixture of NO, a tracer gas, and diluent gas, in constant concentration, through the breathing circuit into lungs. The special gas is delivered into the breathing circuit via a connecting tube. The delivery system is feedback controlled through a tracer gas measured from the expiratory end of the respirator. As the delivery system is controlled by the ventilator, although not so described, one can, thus, conclude that the special gas delivery is pulsatile in nature and synchronous with inspiration flow variations. To minimize the risk for $NO_2$ formation, it is presented as advantageous to lead the special gas mixture connecting tube as close to the patient lungs as possible, even through the endotracheal tube to inside the lungs.

However, the problem of small flows of the special gas remains and is even emphasized. Firstly, the longer the connection tube is, the longer time it will take before the special gas will reach the patient end of the tube when starting the system. An example of a small delivery could be as follows. A 0.5 ppm NO concentration from 1000 ppm source, in a tidal volume of 50 ml is to be delivered in one second. This requires a pulse volume of 0.025 ml. For a connecting tube having diameter 1 mm, this volume will occupy 3 cm in the tube. Secondly, and even worse, during inspiration, when the special gas should be delivered, the pressure within the breathing circuit will increase. The increasing pressure will cause gas compression in the connecting tube preventing the small special gas flow into lungs. During expiration the pressure is relieved and the compressed special gas flows out from the connecting tube directly into the expiration flow and the required therapeutic effect is not achieved. Both of these problems are made worse the smaller the special gas flow is and the longer the connecting tube is. Thirdly, the closer the connection tube or the second gas mixer is to the patient, the worse the solution becomes ergonomically. In another embodiment of EP 640357, the special gas is mixed within the respirator. The $NO_2$ formation may however be increased due to the prolonged reaction time between the special gas and the breathing gas described in an article written by R. Kuhlen et al. entitled "Nitrogen dioxide ($NO_2$) production for different doses of inhaled nitric oxide (NO) during mechanical ventilation with different tidal volumes using the prototypes for the administration of NO." The harmful composites may however be removed from the breathing gas immediately before inhalation by scrubbers as presented in U.S. Pat. No. 5,485,827. Also, some wastage of special gas takes place, since all the breathing gas leaving the respirator does not reach the lungs. Thus the arrangement causes a need for evacuation of the gas exhaled from the respirator. From the point of view of ergonometry, this embodiment is advantageous since no additional equipment near the patient is required. However, the possible need of scrubbers will impair the ergonomy.

U.S. Pat. No. 5,423,313 describes a special gas delivery arrangement to be used in connection with respiratory treatment apparatus comprising similar elements to that of EP 640357. This arrangement differs from EP 640357 from the point of view of the control. Whereas EP 640357 targets for constant concentration of the special gas in the inspired mixture, the system described in U.S. Pat No. 5,423,313 delivers the special gas in pulses independently of the respiratory breath cycle. An advantageous pulse frequency is defined to be 53 Hz. It is claimed that with the high frequency pulses, more even gas distribution is reached in the lungs due to diffusion. However, the high frequency pulses do not change the fact that the total special gas flow range may be very low, and as such, the problems listed for EP 640357 also exist here.

A further NO delivery system is presented in EP 659445. This document also describes an arrangement designed for delivering a constant NO concentration into the inspired breathing gas. It is characteristic of this arrangement that the device can be used with respirator treatment but is not bound to that. A breathing gas flow sensor is included in the equipment. From this sensor, the control unit receives data to regulate the NO gas flow to maintain the required breathing gas concentration. The NO gas is derived from an $NO/N_2$ mixture gas reservoir containing 1000 ppm NO. In the event such a low concentration of NO is required that the system is otherwise unable to reduce the concentration to the desired point, a further equipment in the form of an $N_2$ pressure source, regulating valve, and NO concentration analyzer are provided to further dilute the NO mixture concentration, thus adding gas volume to the NO mixture flow to be regulated. The increasing flow decreases also the described problems caused by the ventilatory pressure variations and the outlet channel volume filling, but does not eliminate same.

BRIEF SUMMARY OF THE PRESENT INVENTION

The object of the present invention is to provide apparatus for mixing a special gas with breathing gas. This special gas may be a therapeutic gas, such as NO supplied in predetermined mixture with $N_2$, or diagnostic gas, such as $SF_6$ (sulphur hexa fluoride) or $N_2O$.

Another object of the present invention is to provide an apparatus for mixing special gas with breathing gas optimizing usage of the special gas to minimize the special gas consumption and to reduce the environmental contamination either with the special gas or in connection with its reaction products with other gases.

A further object of the invention is the provision of an apparatus for mixing special gas with breathing gas that makes the interaction time between the special gas and the breathing gas before it is inhaled by the patient as short as possible.

Yet another object of the invention is the provision of an apparatus for mixing even the smallest required amounts of special gas with breathing gas even under the worst case breathing circuit pressure variations.

The apparatus of the invention is also designed to be ergonomic in use. To reach this objective, the equipment in the central working area near the patient mouth or throat is minimized.

The desired effects of the special gas mixed with the breathing gas take place in definitive gas dependent areas in the lungs. According to the invention, to optimize the usage of the special gas, the special gas is mixed with the breathing gas at the point in time when the breathing gas flowing to the target area of the lungs passes a special gas delivery point in the apparatus. As an example, the NO diffusion from the lungs into the pulmonary capillary circulation takes place in the alveoli, the deepest section of the lungs. Therefore, the NO mixture is advantageously delivered into the breathing gas inspiratory flow as near the lungs and as rapidly as possible just as the inspiration starts or at the end of expiration.

It is known that the NO is absorbed into the lung tissue and pulmonary circulation very rapidly, and thus will not remain in the breathing gas to react with oxygen. Environmental contamination is also reduced or even eliminated. Mixing the NO with the breathing gas as near the lungs as possible will also minimize the reaction time with the breathing gas oxygen before the NO is absorbed.

The problem arising from the pressure variations in the breathing circuit and small doses of the special gas to be mixed with the breathing gas is solved in the invention by positioning a special gas dosing valve, separating the high pressure (advantageously 0.9–2 bar above ambient pressure) special gas channel, from the breathing circuit pressure, to discharge the gas directly into the breathing circuit without any intermediate volume to be filled with the special gas or to be compressed with the breathing circuit pressure variations.

The working environment around the Y-piece of the breathing circuit, specially between the Y-piece and patient mouth or throat is often very crowded. The patient is often suctioned periodically through the endotracheal tube either through an openable opening provided in the patient limb or simply by detaching the endotracheal tube from the breathing circuit. The patient is also moved, or even moves by himself. The breathing circuit must follow these movements. Thus the weight and amount of equipment on this moveable area should be minimized.

The present invention meets these requirements in an apparatus mixing the special gas with breathing gas. The device doses a user defined volume of special gas synchronously with the patient inhalation flow, the synchronization also being defined by the user. A special gas dosing valve discharges the dose directly into the breathing circuit section essentially at the breathing circuit pressure. The dosing equipment is located at a distance from the patient, advantageously within or near the respirator or the breathing gas source, not to disturb the crowded working environment. The small volume dose of the special gas is dosed to a carrier gas outlet conduit of small diameter, advantageously 0.5–2 mm, located in parallel with the inspiratory conduit. This carrier gas outlet conduit extends from a carrier gas source to the point where the special gas is to be mixed with the breathing gas, advantageously between the breathing circuit Y-piece and patient lungs. Within the carrier gas outlet conduit there is a high speed, though small volume, gas flow. While dosing the special gas into this conduit, the dose is rapidly carried by the carrier gas flow to the breathing gas mixing point. As an example, with a carrier gas outlet conduit of one meter from the dosing point to the mixing point and one millimeter in diameter, a carrier gas flow of 0.5 liter/min will flush the special gas dose into the mixing point in 100 ms, a time frame which is very acceptable in comparison with the total inhalation times, starting most typically from one second up to a couple of seconds. The magnitude of the carrier gas flow is not critical and measuring the flow in the delivery point of view is not essential. Although it may be an advantage in the safety point of view to monitor the carrier gas flow for proper flushing of the special gas. The carrier gas flow is advantageously started at the end of the special gas dosing or simultaneously with the special gas dosing. In the case where reaction between the carrier gas and the special gas may take place, the reaction time is minimized when the special gas and the carrier gas are transported as successive bolus in the carrier gas outlet conduit. The carrier gas flow lasts, in time, advantageously at least the dose flow time through the carrier gas outlet conduit beyond the end of the special gas dose to guarantee the mixing of the whole special gas dose with the breathing gas. The carrier gas flow can be continuous, if desired.

The carrier gas source can be a pressure source, e.g. air or $O_2$. It must be kept in mind, however, that with the smallest tidal volumes, even this smallest carrier gas flow can adversely affect the inhaled gas composition. Further, an additional pressurized source is required.

Advantageously, the carrier gas should have the same composition as the breathing gas to be inhaled. This can be accomplished with a respirator having an additional outlet for breathing gas at elevated pressure by using the additional outlet as the carrier gas flow supply. A more general solution may be achieved when the special gas dosing unit itself includes a carrier gas source in a form of a pump suctioning breathing gas from the inspiratory limb of the breathing circuit and discharging into the carrier gas line. Pumping the breathing gas as the carrier gas with high speed from the inspiratory limb to the patient limb does not affect the breathing gas composition, inhalation tidal volume (because the breathing circuit volume does not change), or inhalation pressure. The only additional equipments needed in the breathing circuit are the carrier gas suctioning connection and the carrier gas line end connection. The first of these can be located in the respirator end of the inspiratory limb. Thus, the only equipment in the working area are the carrier gas outlet conduit end connection and the carrier gas outlet conduit itself. The carrier gas outlet conduit is advantageously on the order of 2 mm outside diameter and the short time the special gas is located within the tubing expands the selection of useable materials. The small and flexible carrier gas outlet conduit is easy to handle and integrating it and its connector with the breathing circuit is ordinary state of the art technology widely utilized already in different kinds of monitoring equipment. The arrangement increases also the reliability of the special gas dosing unit since no sensitive equipment or high concentration-high pressure special gas tubings are located in the working area and thus liable to damage.

In another embodiment of the invention the carrier gas flow can be suctioned during expiration through the same carrier gas outlet conduit through which it is discharged during inspiration. In this case, however, the inspiratory breath volume will be affected due to the changing breathing circuit volume and if the carrier gas outlet conduit is discharging into the patient limb, an increased dead space will take place. Also, the risk of $NO_2$ formation is increased in the case the absorption of NO is not perfect. Alternatively, the carrier gas outlet conduit could discharge into the inspiratory limb, but this will increase the delivery delay for the increased volume from the discharge point to lungs.

Various other features, objects, and advantages of the invention will be made apparent from the following detailed description and the drawings.

DETAILED DESCRIPTION OF THE INVENTION

Figure 1:
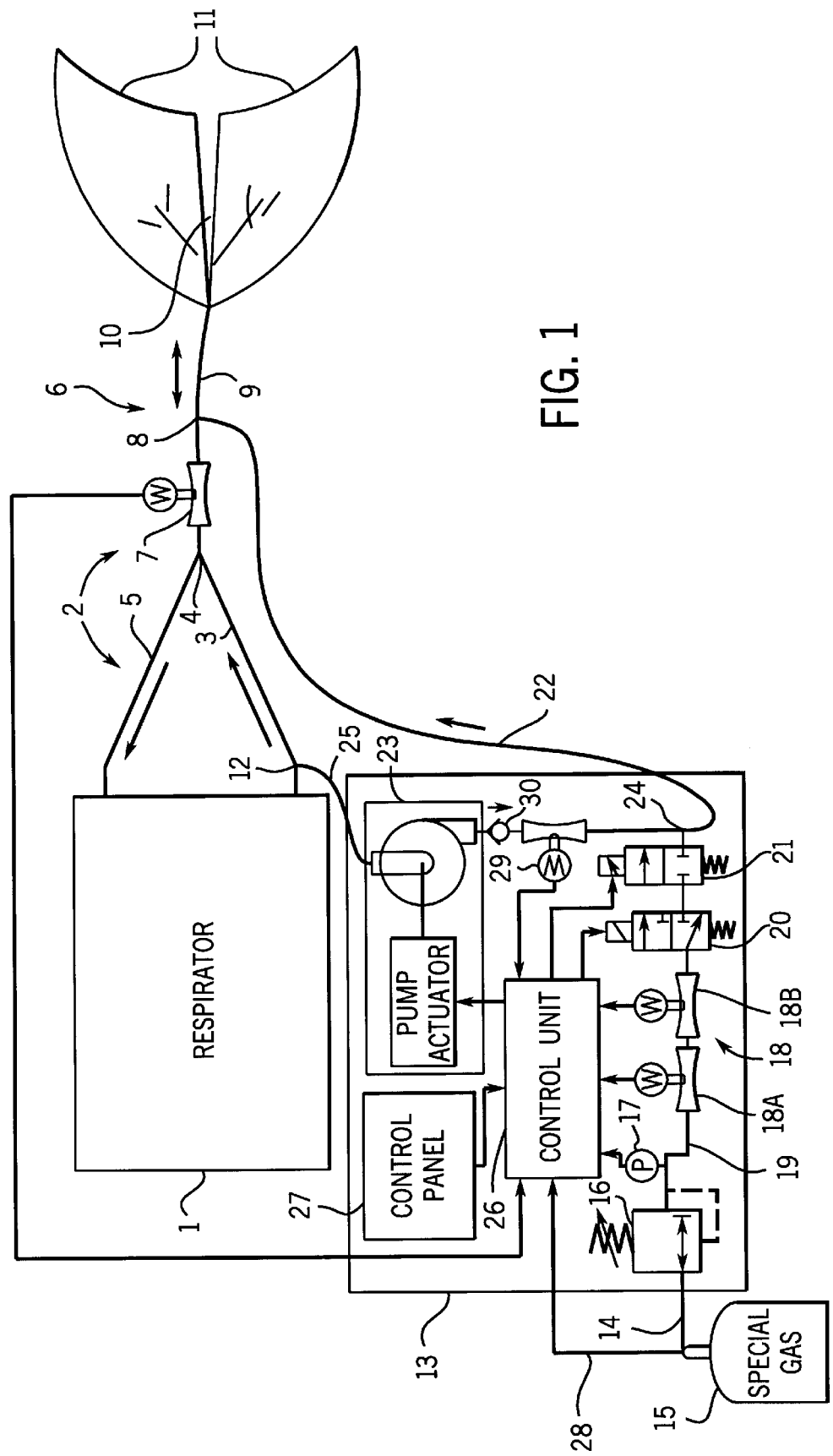
FIG. 1 is a schematic view showing an apparatus of the invention.

In a first embodiment shown in FIG. 1, the respirator 1 is a conventional respirator used to ventilate patient lungs by simulating the spontaneous breath volumes and frequencies. The respirator technology is well known to the extent required herein and will not be described in detail.

The breathing circuit 2 comprises inspiratory limb 3, Y-piece connector 4, expiratory limb 5, and patient limb 6. The inspiratory limb 3 extends from respirator inspiration outlet to Y-piece connector 4 and includes a suction point 12 for the carrier gas flow. The expiratory limb 5 connects the Y-piece connector 4 with the respirator expiration inlet. Included in patient limb 6 are optional flow measuring element 7, carrier gas discharge point 8, and endotracheal tube 9 or a breathing mask forming a conduit from the Y-piece into patient airways 10 and further into lungs 11 of the patient. The breathing circuit may contain also other components for monitoring and therapeutic purposes, such as a humidifier or a filter, depending on the needs of the patient.

The special gas dosing unit 13 is shown separated from the respirator 1, but the two elements could be integrated together if desired. In that case, the control unit of the special gas dosing unit could be the same as that for the respirator control unit. The dosing unit 13 includes an inlet line 14 for the special gas. This conduit connects the high pressure special gas source 15 with a pressure regulator 16. The outlet pressure of pressure regulator 16 is regulated advantageously to at least to 0.9 bar. To monitor the existence and amount of this pressure, a pressure sensor 17 is coupled to the regulated pressure line. The pressure regulator 16 could just as well be located in connection with the special gas as source 15. Pressure regulator 16 is connected to flow measuring unit 18 by flow conduit 19. As shown in FIG. 1, the flow sensing is doubled by connecting two flow sensors in series. This is for supervision purposes, which supervision could also be arranged with some other means. The flow measuring unit 18 discharges the flow into a first valve 20 and further to a dosing valve 21. The dosing valve discharges the special gas into the carrier gas outlet conduit 22 reaching from the carrier gas source 23 to the carrier gas discharge point 8. The discharge of the special gas into the carrier gas takes place at the special gas dosing point 24.

In FIG. 1 there is presented an embodiment of the invention where the carrier gas source 23 is sucking carrier gas flow from the inspiratory limb 3 through suction line 25.

The control unit 26 of the special gas dosing unit 13 is connected with the breathing gas flow sensor 7 located in patient limb 6. As well, the control unit is connected to the sensors 18a and 18b, the valves 20 and 21, and the carrier gas source 23. A further connection of the control unit 26 is with the control panel 27. This control panel is used for providing preset dose related parameters to control unit 26 and optionally also for presenting information on the operation of the special gas dosing unit. In view of the possibility of different kinds of special gases to be delivered, containers for these gases should advantageously be automatically identified. This identification can be e.g. pin code, bar code, magnetic pin indexing, magnetic or electrical memory elements or even gas composition measurement. This identification information from the special gas source 15 to the control unit 26 is transmitted through identification signal line 28.

A flow sensor 29 and a check valve 30 is positioned between carrier gas source 23 and special gas dosing point 24. Flow sensor 29 is used to monitor the carrier gas flow. Although the exact magnitude of this flow is not essential for the operation of the device, for safety reasons it may be essential to guarantee delivery of carrier gas to the patient by monitoring its flow. Check valve 30 controls the direction of carrier gas flow.

The operation of the special gas dosing unit 13 of the present invention will now be described in detail. As the dosing of special gas takes place into the inhaled breathing gas, the control unit 13 is informed of the breathing cycle. This information is transmitted from the breathing gas flow sensor 7 but could as well be derived from the respirator. By having an independent flow sensor, a more universal dosing unit is achieved and the dosing system can be used even with spontaneously breathing patients. The flow sensor could also be located within the inspiratory limb 3.

Through control panel 27 the user can define the special gas dosing related parameters, such as the starting point related to the breath cycle, the end point, or alternatively the duration of the dose, the periodicity in relation to breaths, the dose volume to be delivered per inhalation, or alternatively the special gas concentration in the inspired gas. From the information the control unit 26 obtains from flow sensor 7 and control panel 27, it calculates the desired special gas pulse parameters such as the flow during the pulse, opens the control valve 21 to deliver the pulse, and monitors the delivered pulse volume with the flow sensor 18. Synchronously, with the dose delivery as described above, the special gas control unit also activates the carrier gas source 23 to create the carrier gas flow, unless the carrier gas flow is continuous. This flow may be monitored for safety reasons by flow sensor 29. If the carrier gas flow is not detected, an alarm is given. A check valve 30 is added to direct the special gas dose flow in the correct direction in the case where the carrier gas flow is started after the special gas pulse. This check valve 30 may also be an integral part of the carrier gas source 23. The control valve 21 is advantageously a proportional valve, but alternatively a digitally controlled valve could be used. In the latter case, however, the fact that the flow through the valve may be constant must be considered in controlling its operation.

The valve 20 is a safety backup for the control valve 21. If the flow sensor 18 detects special gas doses in excess of the required dose, the flow can be shut off by the valve 20. Valve 20 may be an ordinary solenoid valve.

The flow sensor 18 is advantageously located at the special gas flow conduit 19 and as near the control valve 21 as possible. Positioning the flow sensor downstream of the control valve 21 would violate the discharge from the control valve 21 directly into the carrier gas line and further, the carrier gas line being essentially at the breathing circuit pressure, the variations in this pressure would cause reciprocating flow through the flow sensor. In the regulated pressure line, the sensor location near the control valve 21 shortens the pneumatic response time from the control valve operation to flow detection by the flow sensor 18.

The special gas regulated pressure is advantageously high enough to fulfill sonic flow conditions in discharging the pressure from the control valve 21 into the carrier gas outlet conduit 22. Fulfilling this criteria makes the special gas dosing insensitive to the pressure variations in the breathing circuit. The carrier gas source 23 is advantageously a pump. Variable types of state of the art pumps can be employed, such as a positive displacement pump. The pump actuator can be e.g. a motor or a coil that provides the movement required by the pump.

Figure 2:
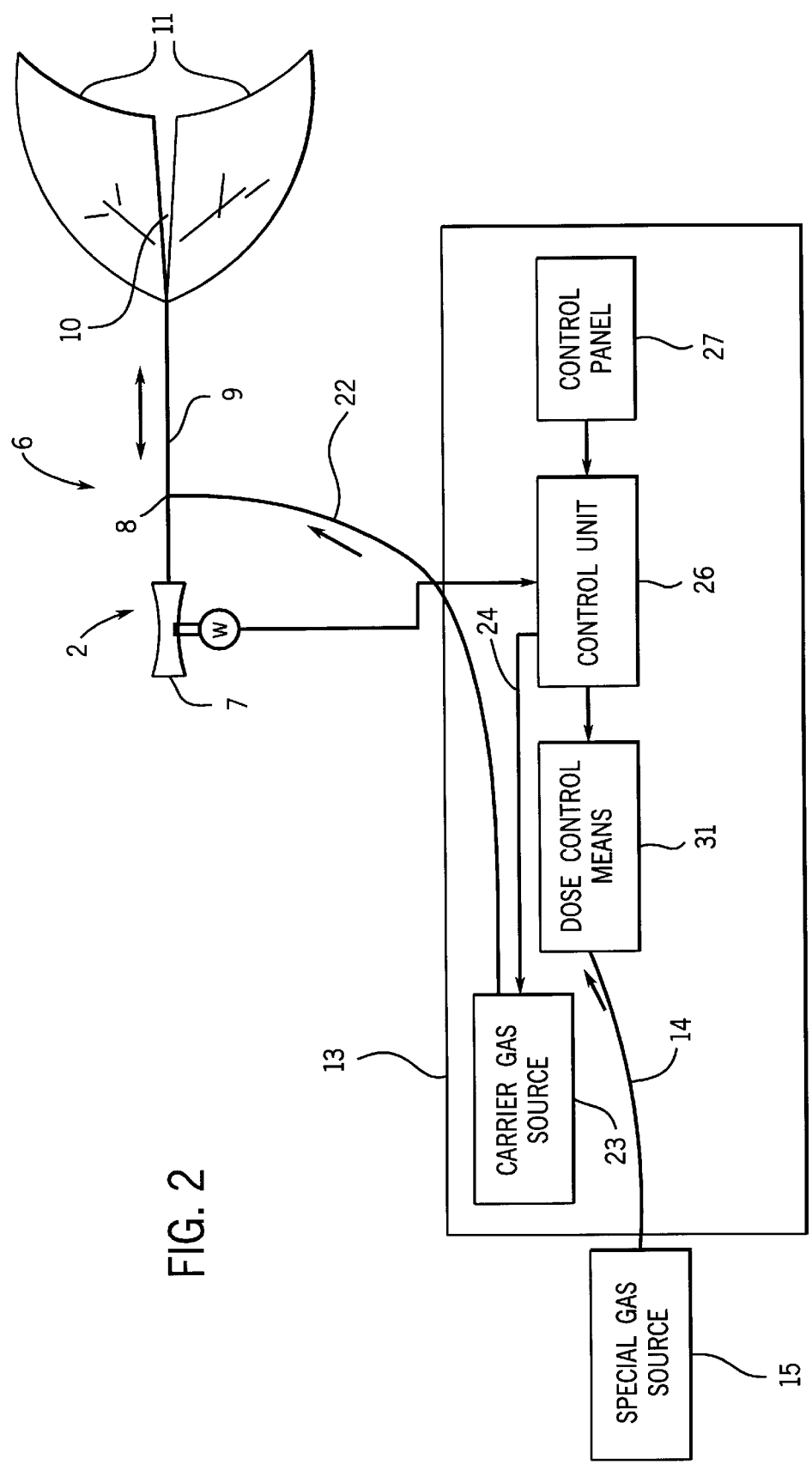
FIG. 2 is a schematic view showing an alternative apparatus of the invention.

A second embodiment of the invention is shown in FIG. 2 for a special gas dose delivery system to be used with spontaneously breathing patients. In this embodiment, there is no respirator, no Y-piece connector, no inspiratory limb and no expiratory limb.

The breathing circuit 2 includes patient limb 6. Included in patient limb 6 are breathing gas flow sensor 7, carrier gas discharge point 8, and endotracheal tube 9 or a breathing mask forming a conduit into patient airways 10 and further into lungs 11 of the patient.

The special gas dosing unit 13 includes an inlet line 14 from a special gas source 15. This special gas inlet line 14 connects the high pressure special gas source 15 to a dose control means 31. The dose control means 31 is the equivalent of the pressure regulator 16, pressure sensor 17, flow sensors 18 and control valves 20, 21, in FIG. 1. The dose control means 31 discharges the special gas into a carrier gas outlet conduit 22. The carrier gas outlet conduit 22 connects from the carrier gas source 23 to the carrier gas discharge point 8. The discharge of the special gas into the carrier gas takes place at the special gas dosing point 24. The carrier gas source 23 is equivalent to the carrier gas source or pump 23 in FIG. 1. The carrier gas source 23 provides the carrier gas to be mixed with the special gas at special gas dosing point 24.

The control unit 26 of the special gas dosing unit 13 is connected with the breathing gas flow sensor 7 located in patient limb 6. Patient breathing cycle information is transmitted from the breathing gas flow sensor 7 to the control unit 26. The control unit is also connected to the dose control means 31 and the carrier gas source 23. A further connection of the control unit 26 is with the control panel 27. This control panel is used for providing preset dose related parameters to control unit 26 and optionally also for presenting information on the operation of the special gas dose control means 31.

High speed gas flow is provided in carrier gas outlet conduit 22 to provide the patient with the special gas very quickly. This is achieved by using a small diameter conduit for carrier gas outlet conduit 22 to increase pressure and thus increase speed. There are differences in the gas line cross-sectional areas between the carrier gas outlet conduit 22 and the breathing circuit conduits 3, 5, and 9. The small volumetric conduit of carrier gas outlet conduit 22 provides the high speed gas flow.

It is recognized that other equivalents, alternatives, and modifications aside from those expressly stated, are possible and within the scope of the appended claims.

I claim:

1. A special gas dose delivery unit for respiration equipment, said respiration equipment having a respirator supplying respiratory gases to a breathing circuit for provision to a patient, said respiration equipment having means for providing an indication of patient respiration, said special gas dose delivery unit comprising:

a flow conduit (19) for the special gas, said flow conduit having one end connectable to a special gas source;

a supply (23) of carrier gas for providing a carrier gas flow in an outlet conduit (22) for the special gas dose delivery unit, said outlet conduit having a discharge end connectable to the breathing circuit, the carrier gas supply having an input connectable to the breathing circuit and means for withdrawing gas from the breathing circuit for obtaining carrier gas for provision to said outlet conduit;

a controllable valve (21) having an inlet connected to said flow conduit and an outlet connected to said outlet conduit, said valve being operable to inject the special gas into the carrier gas flow in the outlet conduit;

means (27) for setting desired parameters of the special gas dose; and a control unit (26), said control unit receiving inputs from the patient respiration indicating means in the respiration equipment and said parameter setting means, said control unit having an output connected to said controllable valve for operating said valve in accordance with said inputs for causing said valve to inject a special gas dose having the desired parameters and timing into the carrier gas for delivery to the patient.

2. The special gas dose delivery unit according to claim 1 wherein the breathing circuit of the respiration equipment has a patient limb and wherein said outlet conduit of said carrier gas supply is further defined as having a discharge end connectable to the patient limb of the breathing circuit.

3. The special gas dose delivery unit according to claim 1 wherein said control unit is further defined as periodically operating said valve to inject a special gas dose into the carrier gas.

4. The special gas dose delivery unit according to claim 3 wherein said carrier gas supply is further defined as coupled to said control unit for providing intermittent carrier gas flow in said outlet conduit and wherein the intermittent provision of the carrier gas is coordinated with the periodic operation of said valve.

5. The special gas dose delivery unit according to claim 1 wherein said carrier gas supply is further defined as providing intermittent carrier gas flow in said outlet conduit.

6. The special gas dose delivery unit according to claim 1 wherein said carrier gas supply is further defined as providing continuous carrier gas flow in said outlet conduit.

7. The special gas dose delivery unit according to claim 1 wherein said withdrawing means comprises a pump.

8. The special gas dose delivery unit according to claim 1 wherein the breathing circuit has an inspiration limb and wherein said carrier gas supply input is connectable to the inspiration limb of the breathing circuit.

9. The special gas dose delivery unit according to claim 1 wherein said carrier gas supply is further defined as providing a flow of carrier gas in said outlet conduit that is sufficiently high to deliver the dose of special gas to the breathing circuit in a desired period of time.

10. The special gas dose delivery unit according to claim 1 wherein said carrier gas supply is further defined as withdrawing gas from the breathing circuit through said outlet conduit during the expiration phase of the patient's respiration.

11. The special gas dose delivery unit according to claim 1 wherein said flow conduit further includes a pressure regulator downstream of said end of said flow conduit connectable to the special gas source.

12. The special gas dose delivery unit according to claim 11 further including a pressure sensor coupled to said flow conduit.

13. The special gas dose delivery unit according to claim 1 further including a gas flow sensor in said flow conduit for the special gas.

14. The special gas dose delivery unit according to claim 13 wherein said flow sensor is located proximate to said controllable valve.

15. The special gas dose delivery unit according to claim 1 further including a gas flow shutoff valve in said gas flow conduit for the special gas, said shutoff valve being operable by said control unit.

16. The special gas dose delivery unit according to claim 1 further including a check valve and a gas flow sensor in said outlet conduit for the carrier gas.

17. The special gas dose delivery unit according to claim 1 further including a gas flow sensor in the breathing circuit for providing the indication of patient respiration.

18. A special gas dose delivery unit for a breathing circuit providing respiratory gases to a patient, said breathing circuit having means for providing an indication of patient respiration, said special gas dose delivery unit comprising:

a flow conduit for the special gas, said flow conduit having one end connectable to a special gas source;

a supply of carrier gas having an input connectable to the breathing circuit and means for withdrawing gas from the breathing circuit for obtaining carrier gas for providing a carrier gas flow in an outlet conduit for the special gas dose delivery unit, said outlet conduit having a discharge end connectable to the breathing circuit;

a controllable valve having an inlet connected to said flow conduit and an outlet connected to said outlet conduit, said valve being operable to inject the special gas into the carrier gas flow in the outlet conduit;

means for setting desired parameters of the special gas dose; and a control unit, said control unit receiving inputs from the patient respiration indicating means in the breathing circuit and said parameter setting means, said control unit having an output connected to said controllable valve for operating said valve in accordance with said inputs for causing said valve to inject a special gas dose having the desired parameters and timing into the carrier gas for delivery to the patient.

19. The special gas dose delivery unit according to claim 18 wherein the breathing circuit has a patient limb and wherein said outlet conduit of said carrier gas supply is further defined as having a discharge end connectable to the patient limb of the breathing circuit.

20. The special gas dose delivery unit according to claim 18 wherein said control unit is further defined as periodically operating said valve to inject a special gas dose into the carrier gas.

21. The special gas dose delivery unit according to claim 20 wherein said carrier gas supply is further defined as coupled to said control unit for providing intermittent carrier gas flow in said outlet conduit and wherein the provision of the carrier gas is coordinated with the operation of said valve.

22. The special gas dose delivery unit according to claim 18 wherein said carrier gas supply is further defined as providing intermittent carrier gas flow in said outlet conduit.

23. The special gas dose delivery unit according to claim 18 wherein said carrier gas supply is further defined as providing a flow of carrier gas in said outlet conduit that is sufficiently high to deliver the dose of special gas to the breathing circuit in a desired period of time.

24. A method for supplying a special gas dose to a breathing circuit of a patient, the breathing circuit supplying a flow of breathing gas to the patient, said method comprising the steps of:

flowing a special gas through a flow conduit from a special gas source;

extracting a portion of the flow of breathing gas from the breathing circuit and supplying the extracted portion of breathing gas into an outlet conduit to provide a carrier gas flow in the outlet conduit;

indicating patient respiration characteristics;

establishing the desired parameters of a special gas dose;

operating a flow regulating valve in the flow conduit to inject the special gas dose into the carrier gas flow in the outlet conduit in accordance with the patient respiration characteristics and the desired dose parameters; and returning the carrier gas to the breathing circuit along with the injected dose of special gas.

25. The method according to claim 24 wherein the step of operating the valve is further defined as periodically operating the valve to inject a special gas dose into the carrier gas flow.

26. The method according to claim 24 wherein the step of supplying the extracted portion of breathing gas is further defined as providing intermittent carrier gas flow in said outlet conduit.

27. The method according to claim 24 wherein the step of supplying the extracted portion of breathing gas is further defined as providing continuous carrier gas flow in said outlet conduit.

28. The method according to claim 24 wherein the step of flowing a special gas through a flow conduit is further defined as sensing the flow of special gas in said flow conduit and interrupting the flow of special gas into the outlet conduit if the sensed flow of special gas exceeds a Predetermined value.

29. The method according to claim 24 wherein the step of supplying the extracted portion of breathing gas in said outlet conduit is further defined as providing a flow of carrier gas in said outlet conduit that is sufficiently high to deliver the dose of special gas to the breathing circuit in a desired period of time.

30. The method according to claim 24 wherein the step of extracting a portion of the flow of breathing gas is further defined as withdrawing a portion of the flow of breathing gas from the breathing circuit such that the carrier gas flow rate is greater than the flow rate of the breathing gas in the breathing circuit.

\* \* \* \* \*